United States Patent [19]

Senkan

[11] Patent Number: 4,983,783
[45] Date of Patent: Jan. 8, 1991

[54] REDUCTION IN CARBON OXIDES IN OXIDATIVE PYROLYSIS OF HALOGENATED METHANES

[75] Inventor: Selim M. Senkan, Chicago, Ill.

[73] Assignee: Illinois Institute of Technology, Chicago, Ill.

[21] Appl. No.: 385,009

[22] Filed: Jul. 25, 1989

[51] Int. Cl.$^5$ .............................................. C07C 1/00
[52] U.S. Cl. .................................. 585/641; 585/540; 585/943
[58] Field of Search ................ 585/325, 540, 641, 943

[56] References Cited

U.S. PATENT DOCUMENTS

| | | | |
|---|---|---|---|
| 2,320,274 | 5/1943 | Gorin | 585/641 |
| 2,488,083 | 11/1949 | Gorin | 585/642 |
| 2,692,902 | 10/1954 | Pichler | 585/943 X |
| 2,964,551 | 12/1960 | Woolcock | 585/943 X |
| 3,234,300 | 2/1966 | Howard | 585/943 X |
| 3,563,709 | 2/1971 | Staud et al. | 585/921 X |
| 4,199,533 | 4/1980 | Benson | 585/500 |
| 4,714,796 | 12/1987 | Senkan | 585/328 |
| 4,724,272 | 2/1988 | Raniere et al. | 585/540 X |
| 4,804,297 | 2/1989 | Minet et al. | 585/641 X |

OTHER PUBLICATIONS

"Conversion of $CH_4$ into $C_2H_2$ and $C_2H_4$ by the Chlorine-Catalyzed Oxidative-Pyrolysis (CCOP) Process 1. Oxidative Pyrolysis of $CH_3Cl$", A. Granada, S. B. Karra, and S. M. Senkan, Ind. Eng. Chem. Res., vol. 26, No. 9, pp. 1901-1905, (1987).

"Converting Methane by Chlorine-Catalyzed Oxidative Pyrolysis", S. M. Senkan, Chemical Engineering Progress, pp. 58-61, Dec. 1987.

Weissman, M. and Benson, S. W., "Pyrolysis of Methyl Chloride, a Pathway in the Chlorine-Catalyzed Polymerization of Methane", In J. Chem. Kinetics, vol. 16, pp. 307-333, (1984).

Primary Examiner—Curtis R. Davis
Assistant Examiner—William Diemler
Attorney, Agent, or Firm—Thomas W. Speckman; Douglas H. Pauley

[57] ABSTRACT

Reduction of carbon oxides products in oxidative pyrolysis of halogenated methanes in gas phase halogen-catalyzed oxidative-pyrolytic, non-flame, conversion of methane to higher molecular weight hydrocarbons is carried out in the presence of oxygen-containing gas which is primarily introduced in a latter portion of the process sequence reducing the oxygen requirement for effective suppression of formation of carbonaceous deposits thereby reducing carbon oxides product. Conversion of halogenated methanes to high yields of ethylene by conduct of the reaction in the presence of methane further reduces oxygen requirements and results in insignificant solid carbonaceous deposit formation.

26 Claims, No Drawings

4,983,783

REDUCTION IN CARBON OXIDES IN OXIDATIVE PYROLYSIS OF HALOGENATED METHANES

BACKGROUND OF THE INVENTION

1. Field of the Invention

This invention relates to reduction in carbon oxides products in oxidative pyrolysis of halogenated methanes in gas phase halogen-catalyzed oxidative-pyrolytic, non-flame, conversion of methane to higher molecular weight hydrocarbons carried out in the presence of oxygen-containing gas which is primarily introduced in a latter portion of the process sequence to reduce the oxygen requirement for effective suppression of the formation of carbonaceous deposits and carbon monoxide.

2. Description of the Prior Art

Natural gas contains varying quantities of methane, typically about 75 weight percent, and thus constitutes an important raw material for the synthesis of higher molecular weight hydrocarbons. Various processes are known for the conversion of methane into acetylene, ethylene and hydrogen using high temperature pyrolysis. However, thermal decomposition of methane results in solid carbonaceous deposits which reduces the yields for desired hydrocarbon products. The reduction of formation of carbonaceous deposits, such as tars, solid carbon and soot, while maintaining high yield for the desired hydrocarbon products, is obtained by oxidative pyrolysis of halogenated methanes in the gas phase and under non-flame conditions in the presence of oxygen as described in U.S. Pat. No. 4,714,796, which is incorporated herein by reference in its entirety. The 4,714,796 patent teaches that as halogenated methane conversion is increased, the molar ratio of ethylene to acetylene in the product decreases at long reaction times. However, since the feed initially did not contain any ethylene its concentration must have earlier increased in the process. Under the conditions of Example 1 of that patent, ethylene to acetylene molar ratio changed from less than about 2 to less than about 1 along the reactor length. Similar molar ratios of ethylene to acetylene product are reported in "Conversion of $CH_4$ into $C_2H_2$ and $C_2H_4$ by the Chlorine-Catalyzed Oxidative-Pyrolysis (CCOP) Process 1. Oxidative Pyrolysis of $CH_3Cl$", A. Granada, S. B. Karra, and S. M. Senkan, Ind. Eng. Chem. Res., Vol. 26, No. 9, pgs. 1901-1905 (1987) and in "Converting Methane by Chlorine-Catalyzed Oxidative Pyrolysis", S. M. Senkan, Chemical Engineering Progress, pgs. 58-61, December 1987. The 4,714,796 patent teaches that carrier gases or mixtures may be used to reduce the concentration of the active reactants and that inert carrier gas may be used, or other gases which do not contain interfering compounds may be used. The 4,714,796 patent teaches that methane or any gaseous source of methane may be used as a carrier gas. Although the 4,714,796 patent teaches the production of ethylene and acetylene from methane by oxidative pyrolysis of halogenated methanes, the carbon oxides also form in the process. Since ethylene is presently a much more valuable product, development of a process providing lower carbon oxides production while maintaining low levels of carbonaceous deposits is desirable.

In a related investigation, Weissman and Benson studied the kinetics of high temperature non-oxidative pyrolysis of methyl chloride under non-flame conditions reporting formation of significant amounts of carbon. Weissman and Benson also teach that increase in methane presence causes significant increase in carbon formation. Weissman, M. and Benson, S. W. "Pyrolysis of Methyl Chloride, a Pathway in the Chlorine-Catalyzed Polymerization of Methane", In. J. Chem. Kinetics, Vol. 16, p. 307-333 (1984).

SUMMARY OF THE INVENTION

This invention provides a process for producing higher molecular weight hydrocarbons from a gas containing halogenated methanes by oxidatively pyrolyzing halogenated methanes under non-flame conditions in the presence of oxygen-containing gas which is primarily introduced in a latter portion of the process sequence thereby reducing the oxygen requirement for effective suppression of formation of carbonaceous deposits and reducing carbon oxides, primarily carbon monoxide, product. A minor portion, less than 50 percent, and preferably less than 20 percent, of the total oxygen introduced to the process may be introduced prior to (upstream to) maximum ethylene production. The major portion of the oxygen is introduced to the process at about the stage of maximum ethylene production and downstream therefrom.

The oxygen requirement for effective suppression of formation of carbonaceous deposits may be further reduced by conducting the oxidative pyrolysis of halogenated methanes in the presence of methane to increase ethylene product selectivity while decreasing acetylene product selectivity. This reduced oxygen requirement is due to a shift of maximum ethylene production to a later time in the reaction sequences with increasing $CH_4/CH_3Cl$ ratio. In this embodiment of the process of this invention, methane is present in an initial molar ratio of methane/halogenated methanes of at least about 0.5 to an upper amount which is limited by practical considerations of gas separation, recompression, and recycling costs in the overall process. Present practical considerations suggest the upper limit of the initial molar ratio of methane/halogenated methanes to be about 10. Preferred initial mole ratios of methane/halogenated methanes should be as high as practical governed by overall process economics and are in the order of about 3 to about 7.

The process of this invention reduces the process oxygen requirements while reducing product gas separation requirements. In one embodiment of the process of this invention, selectivity for ethylene formation is increased while selectivity for acetylene formation is decreased with increasing initial molar ratio of methane/halogenated methanes in the reaction system. High ethylene selectivity is economically desirable due to much greater market demand for ethylene than for acetylene and is process-wise desirable since acetylene precursors are also precursors for formation of carbonaceous deposits. Further, the process of this invention introducing a minor portion of oxygen at early process stages and a major portion of the oxygen at later process stages and using increased initial molar ratios of methane/halogenated methanes does not result in formation of significant amounts of carbonaceous deposits.

DESCRIPTION OF PREFERRED EMBODIMENTS

In the process of this invention, oxygen is principally introduced to the reaction system separate from reactant halogenated methane and methane. It is desired to introduce a minor portion, less than about 50 percent, and preferably less than about 20 percent, of the total oxygen introduced to the process significantly prior to, or upstream to, the point of maximum ethylene production. A minor portion of oxygen introduction to early stages of the reaction system includes no introduction of oxygen with the initial reactants. The process of this invention generally is carried out in a tubular flow through reactor with halogenated methanes and methane reactants introduced at one end and product gases removed from the opposite end. A small fraction of the oxygen, required to suppress formation of carbonaceous deposits, preferably less than about 20 percent of the total oxygen may be introduced with reactant halogenated methanes or in an early stage of the process significantly upstream to the point of maximum ethylene formation. Generally in the conduct of the process of this invention ethylene production will peak along the length of the reactor and then begin to fall. Under these conditions, "maximum ethylene formation" means throughout this description and in the claims the area from the peak of ethylene formation and upstream for about 20 percent of the length of the reactor. Under some conditions ethylene product production may still be increasing at the exit of the reactor. Under these conditions of continuing increase of ethylene production, "maximum ethylene production" means throughout this description and in the claims the area from the reactor exit and upstream for about 20 percent of the length of the reactor. When ethylene production does peak along the length of the reactor, it is desired to introduce the major portion of the oxygen to that portion of the reactor from about 10 percent of the reactor length prior to the ethylene peak to the reactor exit.

One manner of achieving the desired oxygen introduction according to this invention is to conduct the process in two stages with the first stage up to maximum ethylene production being carried out in a separate first reactor or a separated first portion of a reactor and the second stage of the process including and following maximum ethylene production being carried out in a second reactor or a second portion of a reactor to which a major portion of the oxygen is introduced. The major portion of the oxygen is preferably introduced in a continuing manner from the area of maximum ethylene production to the product gas exit from the reactor. This may be achieved by any gas manifold introduction system known to the art. Radial introduction of oxygen in a manner to provide a layer of high oxygen content gas along the reactor walls is preferred to prevent reactor wall contact with precursors of carbonaceous deposits. One preferred embodiment is to introduce oxygen through a porous reactor wall, such as porous ceramics as are available, thereby introducing the oxygen radially and maintaining a layer of oxygen along the inner reactor wall at locations where precursors of carbonaceous deposits are present in the product gas stream. In preferred embodiments introduction of oxygen may be increased in specific regions of the reactor where the formation of precursors of carbonaceous deposits takes place as determined by knowledge of kinetics of process reactions.

The process of the present invention may advantageously be carried out in the presence of methane to increase ethylene selectivity while reducing acetylene selectivity, acetylene precursors also being precursors to the formation of carbonaceous deposits. Reduction in precursors to formation of carbonaceous deposits reduces the oxygen requirement for suppression of formation of such deposits. This embodiment of the present invention provides ethylene selectivity, conversion to ethylene, as high as in the order of 60 percent ethylene at 50 percent conversion of chloromethane.

A preferred embodiment may comprise a one or two step process wherein a feedstock gas comprising methane is first converted into halogenated methanes, and oxidative pyrolysis of halogenated methanes is then carried out in the gas phase and under non-flame conditions.

The halogenated methanes used in the oxidative pyrolysis of the invention may include, mono-, di-, tri- and tetra-halogenated methanes. Halogenated methanes may be produced by any suitable method known to the art, such as those referred to in U.S. Pat. Nos. 2,320,274, 2,488,083 and 4,199,533. The halogenation of methane may be carried out in the same reaction vessel or in a reaction vessel separate from the oxidative pyrolysis of this invention.

The oxidative pyrolysis of halogenated methanes according to this invention is carried out at temperatures of about 500° C. to about 1500° C., preferably about 900° C. to about 1200° C., and under pressures of about 0.1 atmosphere to about 50 atmospheres, preferably about 1 atmosphere to about 5 atmospheres. Suitable reaction times are about 0.05 to about 10 seconds, about 0.1 to about 0.5 seconds being preferred. Suitable reaction chambers capable of withstanding the temperature and pressure requirements of the present invention are well known to the art.

The oxidative pyrolysis of halogenated methanes is carried out in the presence of methane which enters into the reaction system to increase selectivity of product ethylene while decreasing selectivity of product acetylene while achieving high halogenated methane conversion without formation of carbonaceous deposits. Suitable initial methane/halogenated methanes molar ratios are greater than 0.5 up to an upper amount limited by considerations of separation, recycle and recompression costs. A practical upper limit of initial methane/halogenated methanes molar ratios s about 10. Preferred initial molar ratios of methane/halogenated methanes are about 3 to about 7. Feedstock gas containing methane, in addition to that required for production of halogenated methanes, suitable for use in the process of this invention may comprise any methane containing gas which does not contain interfering compounds. Preferably, the methane containing gas suitable for use as a feedstock in the process of this invention comprises at least about 25 percent by weight methane and may comprise up to 100 percent by weight methane. Sources of methane containing gas include natural gas, synthetic natural gas (SNG), product gas from gasification of carbonaceous materials, such as gasification of coal, peat, shale, and the like, as well as products of anaerobic digestion of various biomass materials. These gases principally comprise methane and may contain other gases such as ethane, propane, acetylene and ethylene, which produce corresponding chemical reactions to those of methane in the process of this invention. Purification of such mixed gases comprising principally methane is not usually necessary. These sources of methane containing gas and processes for producing methane are well known in the art.

Any source of halogen containing gas which does not contain interfering chemical compounds may be used in the process of this invention. It is preferred that the halogen containing gas contain at least about 25 percent and may contain up to 100 percent by weight halogen selected from the group consisting of chlorine, bromine, iodine, and mixtures thereof. The amount of halogen required depends upon the methane to halogenated methane ratio in the mixture used in the oxidative pyrolysis step. Chlorine is a preferred halogen for use in this invention. Halogen containing gas may be largely supplied by recycle of gas obtained by recovery of the halogen acid which forms in the oxidative pyrolysis process. Such halogen recovery may be by any method known to the art, such as taught by U.S. Pat. Nos. 2,320,274 and 4,199,533. Make-up halogen may be added as required. According to the process of this invention, the gaseous mixture comprising halogenated methanes and oxygen is fed to the oxidative pyrolysis reaction zone in the halogenated methanes/oxygen mole percentage ratios of about 1 to about 100, preferably about 5 to about 20.

Any oxygen containing gas which does not contain interfering chemical compounds and can provide the above specified halogenated methanes/oxygen mole percentage ratios in the particular reaction system are suitable for use in the process of this invention. Also, any oxygen containing precursor compound, such as steam, which under conditions of this process provides oxygen, may be suitable for use in this invention. The term "oxygen containing gas" as used throughout this disclosure and claims refers to gas containing oxygen, such as air or steam, and gases having an oxygen content of up to 100 percent. It is preferred to use oxygen containing gas comprising over about 50 volume percent oxygen.

It is a further requirement of the oxidative pyrolysis process of this invention that the reaction be carried out under non-flame conditions. These non-flame conditions are maintained by selection of temperature, pressure and specific gas ratios which do not lead to flame formation. These conditions can be ascertained by one skilled in the art in view of the above parameters. utilization of broad operating conditions, as set forth above, is rendered possible due to the known flame inhibiting characteristic of halogens and halogenated compounds. Carrier gases or mixtures may be used to reduce the concentration of active reactants. Inert carrier gas may be used, or other gases which do not contain interfering compounds may be used.

In the process system for formation of ethylene in oxidative pyrolysis of halogenated methanes in the presence of oxygen-containing gas under non-flame conditions, increased presence of methane is necessary to increase product ethylene selectivity. I have found that under the conditions for non-flame oxidative pyrolysis of halogenated methanes in the presence of oxygen-containing gas that methane reacts with the chlorine radical to form precursors to form increased amounts of ethylene. I have found that the presence of methane in the reaction system under the above specified reaction conditions has not caused formation of carbonaceous deposits. Ethylene selectivity may be increased to greater than about 25 mole percent, based upon halogenated methanes reacted by conducting the process in the presence of methane present in an initial molar ratio of methane/halogenated methanes of greater than about 2. By increasing the initial molar ratio of methane/halogenated methanes to about 3 to about 7, ethylene selectivity is increased to greater than about 30 mole percent while acetylene selectivity is reduced to less than about 20 percent.

The following specific example sets forth details of a preferred embodiment of the process of the present invention for oxidative pyrolysis of monochloromethane in the presence of oxygen and methane. This example uses methyl chloride obtained by chlorination of methane in a first step by any suitable process. The specific example is intended to be illustrative only and is not intended to limit the present invention in any way.

EXAMPLE 1

Oxidative pyrolysis of monochloromethane was carried out in a pressure of about 0.7 atmosphere in a transparent quartz reactor 100 cm. long and having an inner diameter of 2.1 cm. placed in a three zone electric tube furnace. Methane and monochloromethane were introduced into the furnace in the amounts indicated in Table 1 with 2.5 mole percent oxygen and the mixture rapidly heated to about 900° C. The reactant gas mixture of methane, monochloromethane, and oxygen were passed through the reaction zone at a velocity resulting in a mean reaction time of 0.4 seconds.

The products were withdrawn from the reactor and subsequently analyzed by a gas chromatograph, the major species quantified being $C_2H_2$, $C_2H_4$, $C_2H_6$, and CO. Several runs were conducted at the methane/monochloromethane ratios indicated in Table 1.

TABLE 1

| Feed $CH_4/CH_3Cl$ | Product Selectivity* | | |
|---|---|---|---|
| | $C_2H_4$ | $C_2H_2$ | CO |
| 1.91 | 25 | 22 | 5 |
| 3.62 | 37 | 18 | 10 |
| 9.22 | 50 | 17 | 30 |

*Product selectivity based upon $CH_3Cl$ reacted.

Table 1 clearly shows the increase in product selectivity for $C_2H_4$ and the decrease in product selectivity for $C_2H_2$ with increasing $CH_4/CH_3Cl$ ratios in the feed. Remaining carbon forms primarily $CH_4$ and to a lesser extent $C_2H_6$. No visible signs of formation of carbonaceous deposit was observed at the reactor exit after a period of four hours operation.

I have found that oxygen concentration in the process system of this invention has essentially no affect upon ethylene product and acetylene product selectivities and results in an approximately directly proportional increase in carbon monoxide formation. Oxidative pyrolysis of monochloromethane was carried out under the conditions set forth in Example I except a constant feed $CH_4/CH_3Cl$ ration of 3.62 was maintained, the mean reaction time was 0.45 seconds, and the amount of oxygen in the feed varied as specified in Table 2 which shows the results.

TABLE 2

| Feed $O_2$ Mole % | Product Selectivity | | | |
|---|---|---|---|---|
| | $C_2H_4$ | $C_2H_2$ | CO | Unaccounted Carbon* |
| 0 | 34 | 16 | 0 | 50 |
| 1.5 | 35 | 17 | 8 | 40 |
| 2.5 | 37 | 18 | 10 | 35 |
| 3.5 | 40 | 18 | 15 | 27 |
| 4.5 | 36 | 18 | 20 | 26 |

*Predominantly $CH_4$ and small amounts of carbonaceous deposits at lower $O_2$ levels.

Table 2 clearly shows that reduced oxygen requirements of the process system exhibit a proportional reduction in carbon oxides, carbon monoxide product.

Table 2 also shows that unaccounted carbon, that is carbon that cannot be accounted for by the measurement of $C_2H_4$, $C_2H_2$, and CO, decreases with increasing $O_2$. Since unaccounted carbon also is a measure of the extent of the formation of carbonaceous deposits, it is clear that increasing $O_2$ concentration decreases the likelihood of such deposits.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. A method of reducing product carbon oxides in a process oxidatively pyrolyzing halogenated methanes under non-flame conditions in the presence of an oxygen containing gas to produce higher molecular weight hydrocarbons with effective suppression of formation of carbonaceous deposits, said method comprising introducing only a minor portion of oxygen to said process upstream of maximum ethylene formation.

2. A method of reducing product carbon oxides in accordance with claim 1 wherein less than about 50 percent of said oxygen introduced to said process is introduced upstream of maximum ethylene formation.

3. A method of reducing product carbon oxides in accordance with claim 1 wherein less than about 20 percent of said oxygen introduced to said process is introduced upstream of maximum ethylene formation.

4. A method of reducing product carbon oxides in accordance with claim 1 wherein greater than about 50 percent of said oxygen introduced to said process is introduced to the reactor in which said process is conducted in the area from maximum ethylene formation to the product gas exit of said reactor.

5. A method of reducing product carbon oxides in accordance with claim 4 wherein said oxygen is introduced radially into said reactor.

6. A method of reducing product carbon oxides in accordance with claim 4 wherein said oxygen is introduced through a porous sidewall into said reactor.

7. A method of reducing product carbon oxides in accordance with claim 2 wherein temperatures are maintained at about 500° C. to about 1500° C.

8. A method of reducing product carbon oxides in accordance with claim 2 wherein temperatures are maintained at about 900° C. to about 1200° C.

9. A method of reducing product carbon oxides in accordance with claim 2 wherein pressures are maintained at about 0.1 atmosphere to about 50 atmospheres.

10. A method of reducing product carbon oxides in accordance with claim 2 wherein pressures are maintained at about 1 atmosphere to about 5 atmospheres.

11. A method of reducing product carbon oxides in accordance with claim 2 wherein the mole percentage ratio of halogenated methanes to oxygen is about 1 to about 100.

12. A method of reducing product carbon oxides in accordance with claim 2 wherein the mole percentage ratio of halogenated methanes to oxygen is about 5 to about 20.

13. A method of reducing product carbon oxides in accordance with claim 2 wherein the gas residence time is about 0.05 to about 10 seconds.

14. A method of reducing product carbon oxides in accordance with claim 2 wherein the ga residence time is about 0.1 to about 0.5 seconds.

15. A method of reducing product carbon oxides in accordance with claim 2 wherein said halogenated methanes principally comprise monochloromethane.

16. A method of reducing product carbon oxides in accordance with claim 2 wherein said oxygen-containing gas comprises over about 50 volume percent oxygen.

17. A method of reducing product carbon oxides in accordance with claim 2 wherein said oxygen-containing gas comprises steam.

18. A method of reducing product carbon oxides in accordance with claim 1 wherein said process is conducted in the presence of methane present in an initial molar ratio of methane/halogenated methanes of greater than about 0.5 thereby increasing ethylene product selectivity.

19. A method of reducing product carbon oxides in accordance with claim 18 wherein said initial molar ratio of methane/halogenated methanes is about 0.5 to about 10.

20. A method of reducing product carbon oxides in accordance with claim 18 wherein said initial molar ratio of methane/halogenated methanes is about 3 to about 7.

21. A method of reducing product carbon oxides in accordance with claim 18 wherein said initial molar ratio of methane/halogenated methanes is about 0.5 to about 10; temperatures are maintained at about 500° C. to about 1500° C.; pressures are maintained at about 0.1 atmosphere to about 50 atmospheres; the initial mole percentage ratio of halogenated methanes to oxygen is about 1 to about 100; and the gas residence time is about 0.05 to about 10 seconds.

22. A method of reducing product carbon oxides in accordance with claim 18 wherein said initial molar ratio of methane/halogenated methanes is about 3 to about 7; temperatures are maintained at about 900° C. to about 1200° C.; pressures are maintained at about 1 atmosphere to about 5 atmospheres; the initial mole percentage ratio of halogenated methanes to oxygen is about 5 to about 20; the gas residence time is about 0.1 to about 0.5 seconds and said halogenated methanes principally comprise monochloromethane.

23. A method of reducing product carbon oxides in accordance with claim 22 wherein greater than about 50 percent of said oxygen introduced to said process is introduced to the reactor in which said process is conducted in the area from maximum ethylene formation to the product gas exit of said reactor.

24. A method of reducing product carbon oxides in accordance with claim 23 wherein said oxygen is introduced radially into said reactor.

25. A method of reducing product carbon oxides in accordance with claim 18 wherein greater than about 50 percent of said oxygen introduced to said process is introduced to the reactor in which said process is conducted in the area from maximum ethylene formation to the product gas exit of said reactor.

26. A method of reducing product carbon oxides in accordance with claim 18 wherein said oxygen is introduced radially into said reactor.

* * * * *